United States Patent [19]

Tompkins et al.

[11] Patent Number: 5,106,008
[45] Date of Patent: Apr. 21, 1992

[54] LOCKING MECHANISM FOR A SURGICAL FASTENING APPARATUS

[75] Inventors: Thomas M. Tompkins, Trumbull; Dominic F. Presty, Shelton, both of Conn.

[73] Assignee: United States Surgical Corporation, Norwalk, Conn.

[21] Appl. No.: 728,710

[22] Filed: Jul. 11, 1991

Related U.S. Application Data

[63] Continuation of Ser. No. 579,830, Sep. 10, 1990, Pat. No. 5,031,814, and a continuation of Ser. No. 358,421, May 26, 1989, Pat. No. 4,955,959.

[51] Int. Cl.⁵ .................................. A61B 17/072
[52] U.S. Cl. ....................... 227/178; 227/8; 227/19; 227/180
[58] Field of Search ............ 227/8, 19, 175, 178, 227/180

[56] References Cited

U.S. PATENT DOCUMENTS

| | | |
|---|---|---|
| 2,174,219 | 9/1939 | Balma . |
| 2,246,647 | 6/1941 | Vancura . |
| 3,079,606 | 3/1963 | Bobrov . |
| 3,490,675 | 1/1970 | Green et al. . |
| 3,499,591 | 3/1970 | Green . |
| 3,844,289 | 10/1974 | Noiles . |
| 4,086,926 | 5/1978 | Green et al. . |
| 4,202,480 | 5/1980 | Annett ................. 227/8 |
| 4,256,251 | 3/1981 | Moshofsky .............. 227/120 |
| 4,391,401 | 7/1983 | Moshofsky .............. 227/19 |
| 4,473,077 | 9/1984 | Noiles et al. ............ 227/19 X |
| 4,519,532 | 5/1985 | Foslien .................. 227/8 |
| 4,520,817 | 6/1985 | Green ................... 227/19 X |
| 4,569,346 | 2/1986 | Poirier ................. 128/305 |
| 4,576,167 | 3/1986 | Noiles .................. 227/19 X |
| 4,591,085 | 5/1986 | Di Giovanni ............ 227/8 |
| 4,633,861 | 1/1987 | Chow et al. ............. 227/19 X |
| 4,646,745 | 3/1987 | Noiles .................. 227/19 X |
| 4,664,305 | 5/1987 | Blake, III et al. ....... 227/19 |
| 4,809,898 | 3/1989 | Gassner et al. .......... 227/8 |
| 4,892,244 | 1/1990 | Fox et al. .............. 227/8 |

Primary Examiner—Frank T. Yost
Assistant Examiner—Rinaldi Rada
Attorney, Agent, or Firm—Thomas R. Bremer

[57] ABSTRACT

An improved surgical stapling apparatus containing a locking mechanism to prevent reactuation of the apparatus, the locking mechanism comprising a resilient clip having a hook which is engagable with a locking notch on the cam bar retainer. The resilient clip is initially held in a non-engagable position by means of a movable chock. When the stapler is actuated for the first time, the cam bar retainer pushes the chock into a subsequent position where the chock no longer blocks the resilient clip. The resilient clip then moves to a position where the hook is engagable with the locking notch. Once the cam bar retainer is retracted it can no longer be reactuated.

10 Claims, 6 Drawing Sheets

LOCKING MECHANISM FOR A SURGICAL FASTENING APPARATUS

This is a continuation of U.S. application Ser. No. 579,830, filed Sept. 10, 1990, now U.S. Pat. No. 5,031,814, which is a continuation of Ser. No. 358,814, filed May 26, 1989, now U.S. Pat. No. 4,955,959.

BACKGROUND OF THE INVENTION

1. Field of the Invention

This invention relates to surgical fastening apparatus and specifically to an improved surgical fastening apparatus containing a locking means.

2. Background of the Prior Art

Surgical fastening apparatus for placing gastro intestinal anastomoses are known in the art. Such apparatus are used for suturing gastric and intestinal walls with spaced parallel rows of longitudinally aligned staples or surgical fasteners. For example, Bobrov et.al. (U.S. Pat. No. 3,079,606) discloses an instrument for suturing gastric and intestinal walls with metal staples by inserting the tips of the instrument into the lumens of the organs to be sutured through apertures in the walls of the organs. The apparatus comprises a two part frame, each part having finger like projections or forks which are inserted respectively into the apertures in the walls of the organs to be sutured. The frame parts are hinged together with the body tissue held between the forks. When the instrument is actuated, longitudinally moving cam bars contact staple staples through the body tissue and into an anvil the opposite fork. A knife blade between the cam bars creates an incision between the parallel rows of staples. It should be noted, however, that the knife blade is an optional feature. The instrument may be used to fasten body tissue without creating an incision between the rows of staples.

Green et.al. (U.S. Pat. No. 3,490,675) discloses an improved instrument of type discussed above, the improved instrument laying down double rows of staples on each side of the incision.

A further improvement in this type of instrument is disclosed in Green (U.S. Pat. No. 3,499,591). The further improved apparatus incorporates an improved structure for the staple-containing cartridge, the pusher assembly which includes the cam bars and knife, and the staple driving members. The contents of the above mentioned patents are incorporated by reference herein in their entirety.

Generally, the instruments discussed above are successfully used in abdominal, gynecological, pediatric and thoracic surgery for resection, transection and creation of anastomoses. However, there is a danger during an operation that the surgeon may inadvertently insert the forks of the instrument into body organs when the instrument is empty of staples. This can occur when the instrument has already been fired but not reloaded or discarded. Under such circumstances, the cam bar and knife blade can be moved, thereby creating an unsealed incision, and causing blood loss and trauma to the patient undergoing the surgery. Non-cutting fasteners, i.e., those without the optional knife mechanism, are also commonly used to seal incisions, for example, in transactions in which the surgeon uses a scalpel to manually create an incision on the outside of the rows of staples. Consequently, the danger of using an empty fastener applies equally to both cutting and non-cutting fasteners. The surgical fastening apparatus mentioned above do not possess means for preventing the blem of reactuation of an apparatus which is empty of staples.

To eliminate these dangers it is beneficial to have a locking mechanism which will allow a single use, but which will prevent the surgical stapler from being inadvertently fired more than once.

SUMMARY OF THE INVENTION

Accordingly, it is one object of the present invention to provide a surgical fastening apparatus. It is another object of the present invention to provide an improved surgical fastening apparatus having a locking mechanism for preventing reactuation of the apparatus.

These and further objects are achieved herein by providing a surgical fastening apparatus including a single use locking mechanism to prevent reactuation of the surgical fastening apparatus, said surgical fastening apparatus comprising:

(a) a frame;

(b) a stationary carrier receivable into said frame;

(c) a pusher assembly slidably mounted within said stationary carrier, said pusher assembly comprising at least one cam bar, a cam bar retainer for mounting the cam bar, said cam bar retainer having a locking notch, a thrust knob attached to the cam bar retainer and optionally a knife mounted to the cam bar retainer;

(d) a resilient locking clip fixed to the stationary carrier and having a hook, said locking clip being adapted to be resiliently urged from a first position wherein said hook is non-engagable with said locking notch, to a second position wherein said hook is engagable with said locking notch; and, (e) a blocking means, adapted to be movable from a location wherein said blocking means holds said locking clip in said non-engagable first position to a location wherein said blocking means does not hold said locking clip in the non-engagable first position.

DETAILED DESCRIPTION OF THE INVENTION

Figure 1:
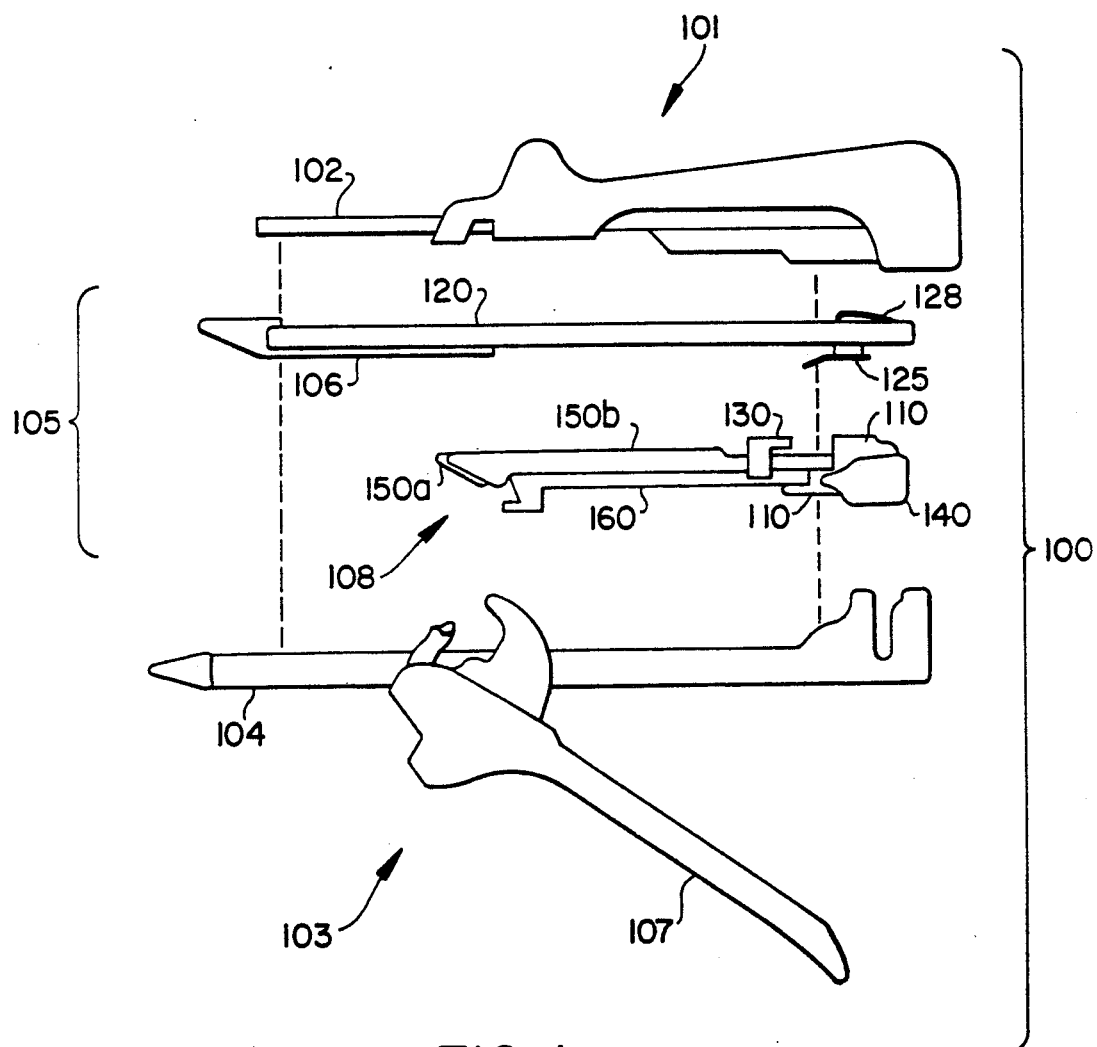
FIG. 1 illustrates an exploded side view of the surgical fastener.
Figure 2:
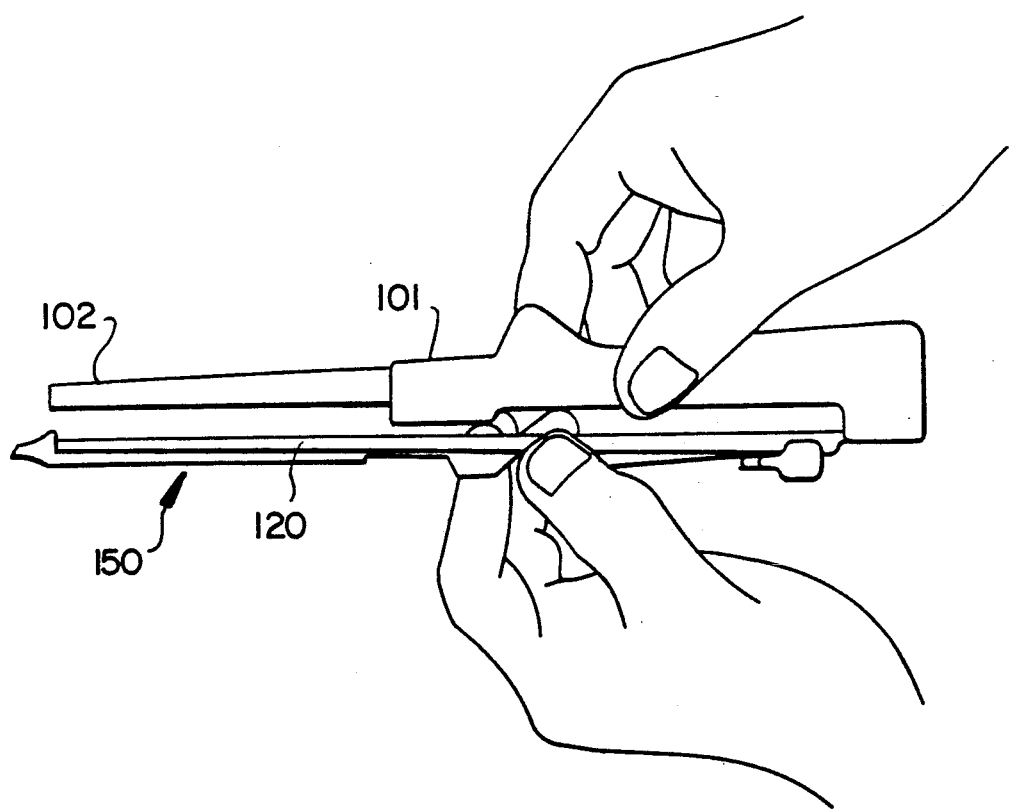
FIG. 2 illustrates the placement of the removable carrier within the surgical fastener.
Figure 3:
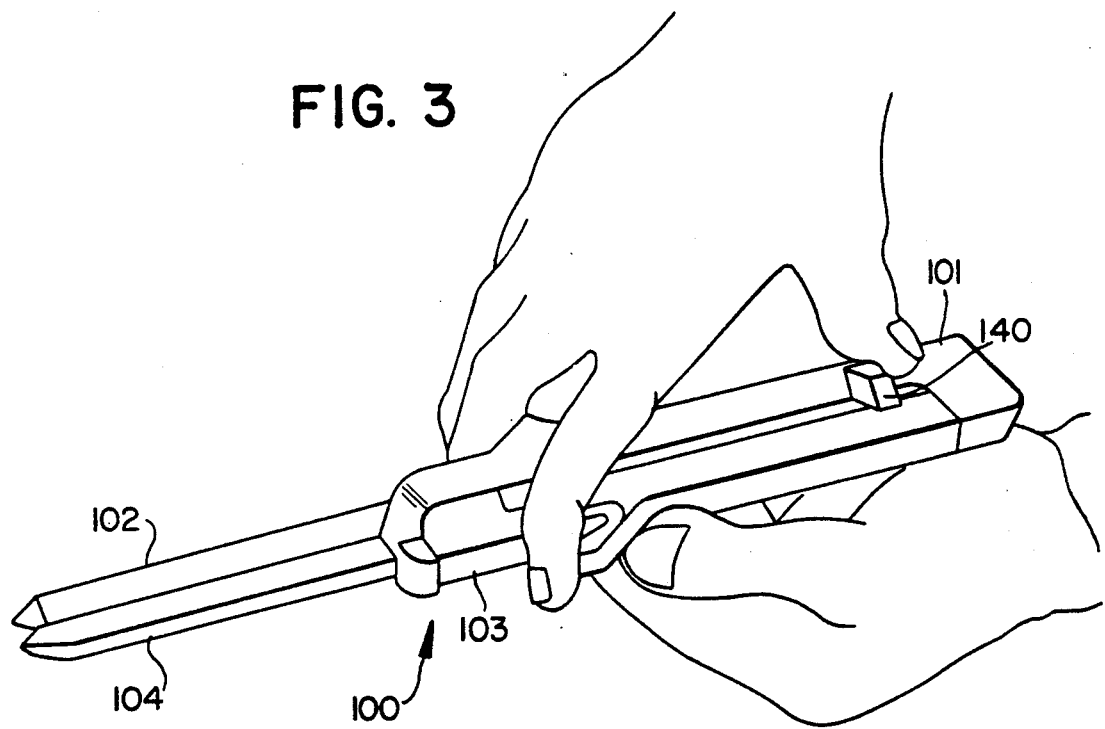
FIG. 3 illustrates the manual operation of the surgical fastener.

FIGS. 1, 2 and 3 illustrate a surgical fastening apparatus for placing gastrointestinal anastomoses. Surgical fastening apparatus 100 is composed of a cartridge half of a frame 101 having a cartridge fork 102, an anvil half of a frame 103 having an avail fork 104 and a pivotable large handle 107, and a disposable loading unit 105 comprising a cartridge assembly 106 (which carries the surgical staples), a stationary carrier 120, and a slidable pusher assembly 108 which includes cam bars 150a, 150b, cam bar retainer 110, optional knife 160, chock 130 and thrust knob 140. The disposable loading unit 105 is loaded into the cartridge half of the frame 101 as shown in FIG. 2, the instrument is assembled, and actuated as shown in FIG. 3 (body tissue to be fastened is not, illustrated).

Figure 4:
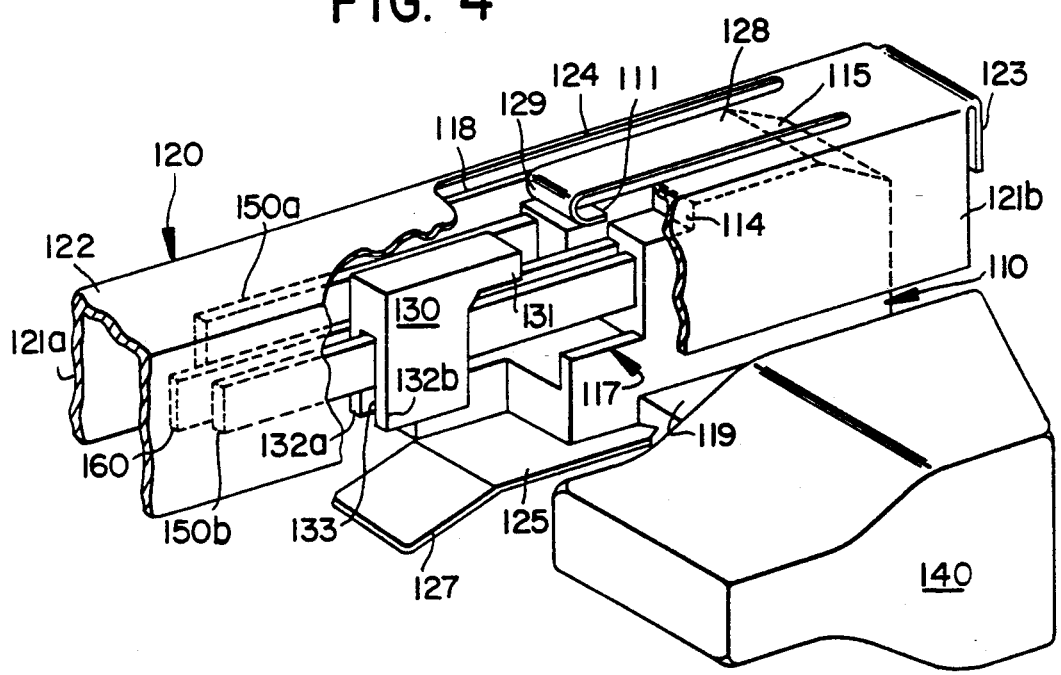
FIG. 4 illustrates a cut-away perspective view of the locking mechanism in the locked position.
Figure 5:
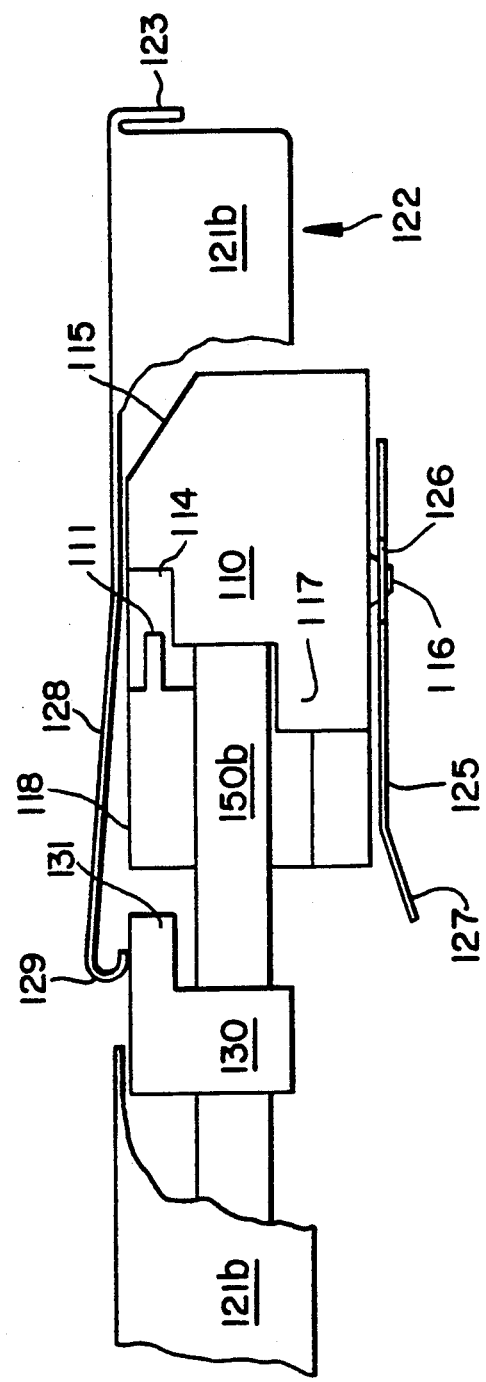
FIG. 5 illustrates a side view of the lock mechanism in the unlocked position. The arm and thrust knob are not shown; and, FIG. 6 illustrates a cut-away perspective view of the locking mechanism. The cam bars, knife, and sliding chock are not shown.
Figure 6:
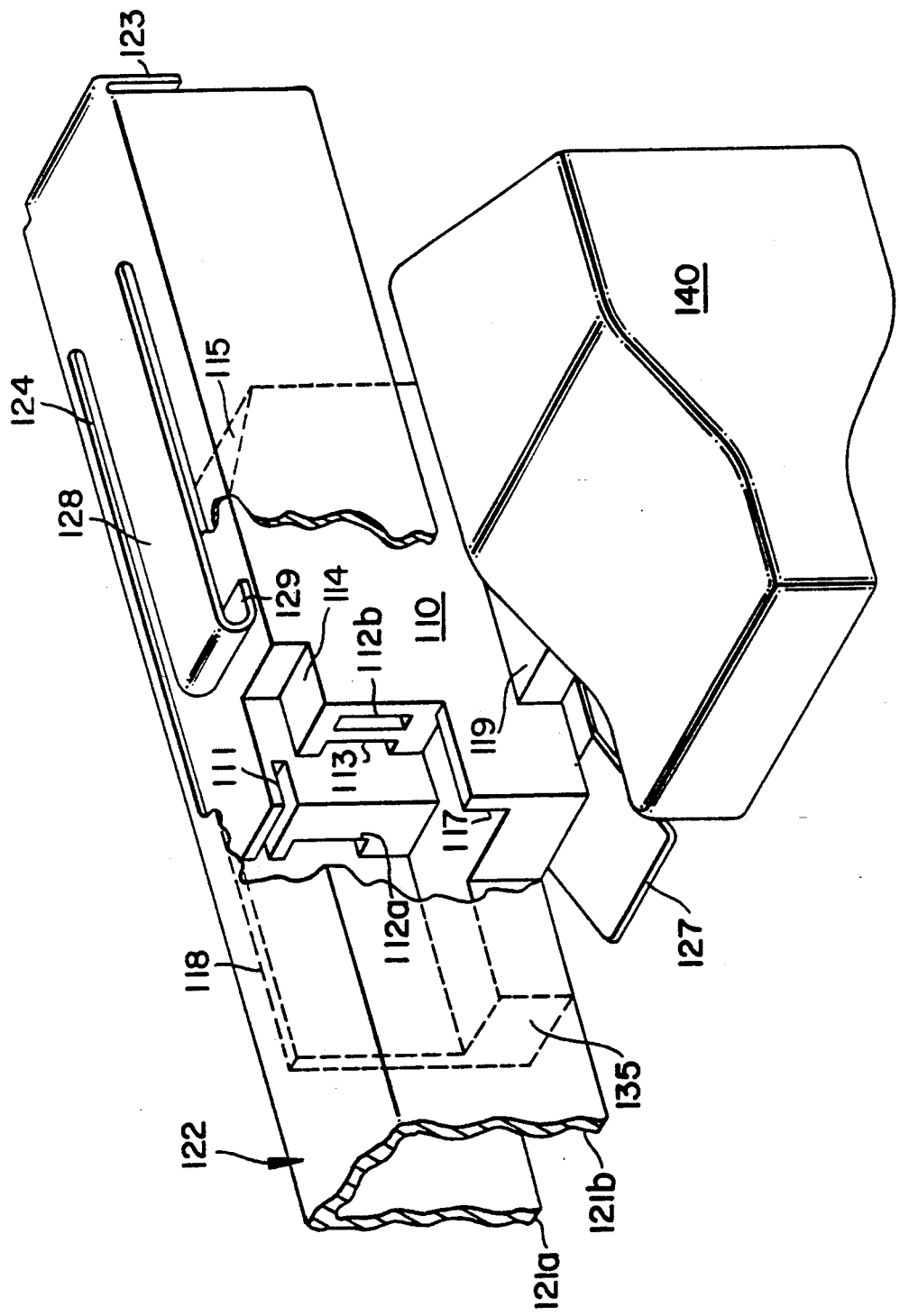

FIGS. 4, 5 and 6 illustrate a single use locking mechanism to prevent reactuation of the surgical stapling apparatus. Stationary carrier 120 is an elongated metal piece having a substantially U-shaped cross section with a base 122 and sidewalls 121a and 121b. Stationary carrier 120 as adapted to fit into a surgical stapler as shown in FIGS. 1, 2 and 3. At its proximal end, stationary carrier 120 has a backflap 123 to prevent the sliding pusher assembly from exiting the instrument. Base 122 has an opening 124 of generally U-shape. Tongue shaped resilient spring clip 128 is attached at its proximal end to base 122 and defines the inner perimeter of the opening 124. Clip 128 is optimally an integral part of the carrier 120. Hook 129 at the distal end of resilient clip 128 curves back in the proximal direction. Optimally, clip 128 is a planar strip which is resiliently bendable in a direction transverse to its plane. Stationary carrier 120 also has a catch plate 125 with guide slope 127 and, as shown in FIG. 5, an aperture 126 for engaging circular detent 116 as explained below.

The surgical fastening apparatus of the present invention also comprises a slidable pusher assembly located within the stationary carrier. The slidable pusher assembly is composed of one or more cam bars 150a, 150b, optionally a knife 160, a cam bar (and knife) retainer 110, and a thrust knob 140. When the instrument is actuated the cam bars will be longitudinally moved through a cartridge assembly, thereby firing the staples.

Cam bar retainer 110 is a solid member, preferably constructed of a strong polymeric resin, which serves as a mounting for the cam bars 150a and 150b and knife 160. Slot 112a in the cam bar retainer receives cam bar 150a, slot 112b receives cam bar 150b, and slot 113 receives knife 160. Cam bar retainer 110 has a horizontal locking notch 111 at its distal end for engaging hook 129. Large and small shoulders, 118 and 117 ride longitudinally within stationary carrier 120. Front face 135 of large shoulder 118 acts as a stop when cam bar retainer 110 reaches the proximal end of cartridge 106. Cam bar retainer 110 has a shelf 114 for engaging the overhang 131 of the chock 130. Backslope 115 enables the cam bar retainer to be easily retracted to the original position in the proximal end of stationary carrier 120. Cam bar retainer 110 also has a circular detent 116 which is received into aperture 126 of catch plate 125. The detent keeps the cam bar retainer 110 secured from accidental firing during shipping and handling. However, the operating surgeon can easily override it manually when pushing on the thrust knob. Arm 119 extends outward from the cam bar retainer 110 and is optimally an integral piece thereof. Thrust knob 140 is attached to arm 119 and provides a means for manually actuating the slidable cam assembly.

Chock 130 provides a blocking means to block or bar the locking clip 128 from resiliently bending into a position wherein hook 129 can engage locking notch 111 of the cam bar retainer 110. Chock 130 is slidably mounted on cam bar 150b, and has two depending legs 132a and 132b, which define a slot 133 for riding on the cam bar 150b. Chock 130 also has an overhang 131 adapted to engage shelf 14 of the cam bar retainer 110. The outward facing surface of chock 130 contacts the inner surface of sidewall 121b, particularly along the outwardly facing surface of depending leg 132b.

The single use locking mechanism is initially in the position as shown in FIG. 5. (The arm and thrust knob are not shown.) The freely slidable chock 130 rests on cam member 150b and is located under the hook 129 of resilient clip 128. In this position hook 129 cannot engage notch 111 of the cam bar retainer 110 because the chock holds the locking clip 128 in a position where said hook 129 is not longitudinally aligned with the notch 111. To actuate the instrument, the surgeon presses on the thrust knob 40 with sufficient force to override the cooperation between detent 16 and catch plate 125, e.g., by shearing off detent 116 or deflecting catch plate 125 away from detent 116. The pusher assembly 108 slides distally in carrier 120 whereupon cam bar retainer 110 engages chock 130 and pushes it to the distal end of the carrier 120. A viscous lubricant on the inside surface of sidewalls 121a and 121b facilitates the sliding movement. The chock scrapes most of the lubricant off the inner surface of side wall 121b as it passes, thereby increasing the frictional resistance to returning to its original position. When the staples are fired the thrust knob 140 is pulled proximally and the cam bar retainer is drawn back into the initial position. Rear sloping surface 115 enables it to pass the resilient clip. The chock 130 is not drawn all the way back, however, in part because of the increased friction with side wall 121b, and chock 130 remains in a subsequent location where it no longer abuts locking clip 128. After cam bar retainer 110 moves proximally past clip 128, clip 128 resiliently springs into a position in which hook 129 is engagable with notch 111. If the surgeon inadvertently attempts to reactuate the instrument, the hook 129 and notch 111 will engage and the cam bar retainer 110 will lock, as shown in FIG. 4.

The loading unit 105 containing the stationary carrier 20, cartridge assembly 106, and pusher assembly 108, is optimally disposable. After using one loading unit, the surgeon may replace it with a new loading unit. The two part frame may be reused. However, it is also within the scope of this invention to have an entirely disposable apparatus in which the frame is not meant to be reused.

Generally the stationary carrier is made of metal such as stainless steel. The cam bars and knife are also preferably of stainless steel construction. The cam bar retainer, chock, arm and thrust knob may be made of any suitable high strength polymeric resin such as polycarbonate.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A surgical fastening apparatus comprising:
    a cartridge frame;
    a cartridge removably mounted in said cartridge frame and having a plurality of fastening elements arranged longitudinally from a proximalmost element to a distalmost element, said fastening elements abutting fastening element drive members arranged longitudinally therein;
    a pusher assembly slidably mounted on said cartridge frame for actuating the surgical stapling apparatus to apply fastening elements and cut body tissue, said pusher assembly having a distal end and a proximal end, said distal end including a tissue cutting surface and a fastening element drive member engaging surface for sequentially urging said drive members in a direction substantially perpendicular to the direction of movement of said pusher assembly;

locking means movable in a direction substantially parallel to the direction of movement of said fastening elements, said locking means movable between an engagable position and a disengagable position; and means for biasing said locking means into said disengagable position, said biasing means movable from a first position prior to firing of the fastening elements to a second position upon distal movement of said pusher assembly to an intermediate position to thereby allow subsequent movement of said locking means into said engagable position upon retraction of said pusher assembly, said intermediate position being before firing of the distalmost fastening element.

2. A surgical fastening apparatus as recited in claim 1, wherein said locking means is located proximally of said distal end of said pusher assembly to prevent distal movement of said pusher assembly upon engagement of said locking means.

3. A surgical fastening apparatus as recited in claim 2, wherein said locking means engages a block member to prevent distal movement of said pusher assembly.

4. A surgical fastening apparatus as recited in claim 3, wherein said locking means comprises a resilient hook formed in said cartridge.

5. A surgical fastening apparatus as recited in claim 4, wherein said biasing means comprises a chock for biasing said hook upwardly.

6. A surgical fastening apparatus comprising:
a cartridge frame;
a cartridge removably mounted in said cartridge frame and having a plurality of fastening elements abutting fastening element drive members arranged longitudinally therein;

a pusher assembly slidably mounted on said cartridge frame for movement between a proximal position and distal positions for driving fastening elements and cutting body tissue, said pusher assembly having a knife bar and a pair of cam bars longitudinally movable through said cartridge, said cam bars each having distal ends for sequentially engaging said fastening element drive members to urge said drive members in a direction substantially perpendicular to the direction of movement of said cam bars, said knife bar having a distal end for contacting and cutting body tissue;

a block member positioned in said cartridge frame and cooperating with said pair of cam bars; and locking means movable in a direction substantially parallel to the direction of movement of said drive members, said locking means movable between a disengagable position and an engagable position wherein said locking means is engagable with said block member to prevent subsequent movement of said pusher assembly into said distal positions.

7. A surgical fastening apparatus as recited in claim 6 further comprising biasing means for biasing said locking means into said disengagable position, said biasing means movable from an initial position prior to firing of said fastening elements to a second position upon initial distal movement of said pusher assembly to thereby allow subsequent engagement of said locking means upon retraction of said pusher assembly.

8. A surgical fastening apparatus as recited in claim 7, wherein said locking means comprises a resilient hook.

9. A surgical fastening apparatus as recited in claim 8, wherein said biasing means comprises a chock biasing said hook upwardly.

10. An apparatus as recited in claim 6, said block member includes first and second slots each configure to receive at least a portion of one of said cam bars.

* * * * *